United States Patent

Amos, Jr.

(10) Patent No.: US 9,254,203 B2
(45) Date of Patent: Feb. 9, 2016

(54) DELIVERY DEVICE

(71) Applicant: Boston Scientific Scimed, Inc., Maple Grove, MN (US)

(72) Inventor: Raymond G. Amos, Jr., Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 8 days.

(21) Appl. No.: 13/968,003

(22) Filed: Aug. 15, 2013

(65) Prior Publication Data

US 2014/0052271 A1 Feb. 20, 2014

Related U.S. Application Data

(60) Provisional application No. 61/691,012, filed on Aug. 20, 2012.

(51) Int. Cl.
*A61F 2/82* (2013.01)
*A61F 2/958* (2013.01)
*A61M 25/00* (2006.01)
*A61M 25/01* (2006.01)
*A61M 27/00* (2006.01)
*A61F 2/88* (2006.01)
*A61F 2/04* (2013.01)

(52) U.S. Cl.
CPC .............. *A61F 2/82* (2013.01); *A61M 25/0074* (2013.01); *A61M 25/01* (2013.01); *A61M 27/008* (2013.01); *A61F 2/88* (2013.01); *A61F 2/958* (2013.01); *A61F 2002/048* (2013.01); *A61M 25/0102* (2013.01)

(58) Field of Classification Search
CPC .............. A61F 2/06; A61F 2/82; A61F 2/958
USPC ............................ 623/1.11–1.38, 23.65–23.7
See application file for complete search history.

(56) References Cited

U.S. PATENT DOCUMENTS

| | | |
|---|---|---|
| 550,238 A | 11/1895 | Allen, Jr. |
| 3,695,021 A | 10/1972 | Ormerod et al. |
| 4,503,569 A | 3/1985 | Dotter |

(Continued)

FOREIGN PATENT DOCUMENTS

| | | |
|---|---|---|
| DE | 10155767 A1 | 5/2003 |
| WO | 01/89415 A2 | 11/2001 |
| WO | 2005/102217 A1 | 11/2005 |

OTHER PUBLICATIONS

International Search Report for PCT Patent Application No. PCT/US2003/034214, mailed on Apr. 15, 2004, 4 pages.

(Continued)

*Primary Examiner* — Suzette J Gherbi
(74) *Attorney, Agent, or Firm* — Kacvinsky Daisak Bluni PLLC

(57) ABSTRACT

A medical device includes an elongate member and a delivery member. The elongate member has a retention portion and defining a lumen. The retention portion has a first configuration and a second configuration different than the first configuration. The retention portion is biased to the first configuration. The delivery member has a collapsed configuration and an expanded configuration. The delivery member is configured to be disposed within the lumen of the elongate member to move the retention portion of the elongate member from the first configuration to the second configuration.

19 Claims, 5 Drawing Sheets

(56) References Cited

U.S. PATENT DOCUMENTS

| | | | | |
|---|---|---|---|---|
| 4,531,933 | A | * | 7/1985 | Norton et al. ..................... 604/8 |
| 4,643,716 | A | | 2/1987 | Drach |
| 4,660,560 | A | | 4/1987 | Klein |
| 4,671,795 | A | | 6/1987 | Mulchin |
| 4,681,570 | A | | 7/1987 | Dalton |
| 4,813,925 | A | | 3/1989 | Anderson et al. |
| 4,874,360 | A | | 10/1989 | Goldberg et al. |
| 4,969,458 | A | * | 11/1990 | Wiktor ........................ 623/1.11 |
| 5,057,114 | A | | 10/1991 | Wittich et al. |
| 5,059,169 | A | | 10/1991 | Zilber |
| 5,098,440 | A | | 3/1992 | Hillstead |
| 5,116,309 | A | | 5/1992 | Coll |
| 5,129,910 | A | | 7/1992 | Phan et al. |
| 5,282,860 | A | | 2/1994 | Matsuno et al. |
| 5,514,176 | A | | 5/1996 | Bosley, Jr. |
| 5,531,741 | A | | 7/1996 | Barbacci |
| 5,554,189 | A | | 9/1996 | De La Torre |
| 5,562,641 | A | | 10/1996 | Flomenblit et al. |
| 5,562,678 | A | | 10/1996 | Booker |
| 5,572,819 | A | | 11/1996 | Topinka et al. |
| 5,599,291 | A | * | 2/1997 | Balbierz et al. ..................... 604/8 |
| 5,613,973 | A | | 3/1997 | Jackson et al. |
| 5,647,843 | A | | 7/1997 | Mesrobian et al. |
| 5,681,274 | A | | 10/1997 | Perkins et al. |
| 5,782,916 | A | | 7/1998 | Pintauro et al. |
| 5,789,047 | A | | 8/1998 | Sasaki et al. |
| 5,795,319 | A | | 8/1998 | Ali |
| 5,814,006 | A | | 9/1998 | Planz |
| 5,827,321 | A | | 10/1998 | Roubin et al. |
| 5,944,701 | A | | 8/1999 | Dubrul |
| 5,962,007 | A | | 10/1999 | Cooper et al. |
| 5,964,744 | A | | 10/1999 | Balbierz et al. |
| 6,019,779 | A | | 2/2000 | Thorud et al. |
| 6,027,516 | A | | 2/2000 | Kolobow et al. |
| 6,059,825 | A | | 5/2000 | Hobbs et al. |
| 6,171,338 | B1 | | 1/2001 | Talja et al. |
| 6,214,042 | B1 | | 4/2001 | Jacobsen et al. |
| 6,241,691 | B1 | | 6/2001 | Ferrera et al. |
| 6,258,119 | B1 | | 7/2001 | Hussein et al. |
| 6,306,105 | B1 | | 10/2001 | Rooney et al. |
| 6,332,892 | B1 | | 12/2001 | Desmond et al. |
| 6,416,539 | B1 | * | 7/2002 | Hassdenteufel ............. 623/1.15 |
| 6,458,145 | B1 | | 10/2002 | Ravenscroft et al. |
| 6,506,201 | B2 | * | 1/2003 | Di Caprio et al. ............ 606/192 |
| 6,558,349 | B1 | | 5/2003 | Kirkman |
| 6,569,150 | B2 | | 5/2003 | Teague et al. |
| 6,620,202 | B2 | | 9/2003 | Bottcher et al. |
| 6,648,912 | B2 | | 11/2003 | Trout, III et al. |
| 6,663,660 | B2 | * | 12/2003 | Dusbabek et al. ........... 623/1.11 |
| 6,685,744 | B2 | | 2/2004 | Gellman et al. |
| 6,719,804 | B2 | | 4/2004 | St. Pierre |
| 6,733,536 | B1 | | 5/2004 | Gellman |
| 6,887,215 | B2 | | 5/2005 | McWeeney |
| 6,913,625 | B2 | | 7/2005 | Segura et al. |
| 6,929,664 | B2 | | 8/2005 | Kolb |
| 6,949,125 | B2 | * | 9/2005 | Robertson .................... 623/23.7 |
| 6,976,973 | B1 | | 12/2005 | Ruddell et al. |
| 7,041,139 | B2 | | 5/2006 | Bluni et al. |
| 7,044,981 | B2 | | 5/2006 | Liu et al. |
| 7,166,134 | B2 | | 1/2007 | Datta et al. |
| 7,169,187 | B2 | | 1/2007 | Datta et al. |
| 7,320,674 | B2 | | 1/2008 | Ruddell et al. |
| 7,507,218 | B2 | | 3/2009 | Aliski et al. |
| 7,550,012 | B2 | | 6/2009 | Lavelle |
| 7,914,570 | B2 | * | 3/2011 | Brown ......................... 623/1.22 |
| 8,568,643 | B2 | * | 10/2013 | Gellman .................... 264/279.1 |
| 2001/0053936 | A1 | | 12/2001 | Whitmore |
| 2002/0177899 | A1 | | 11/2002 | Eum et al. |
| 2002/0183852 | A1 | | 12/2002 | McWeeney |
| 2003/0040803 | A1 | | 2/2003 | Rioux et al. |
| 2003/0060870 | A1 | | 3/2003 | Reever |
| 2003/0163204 | A1 | | 8/2003 | Rix |
| 2003/0171708 | A1 | | 9/2003 | Segura et al. |
| 2003/0176831 | A1 | | 9/2003 | Gellman et al. |
| 2003/0181842 | A1 | | 9/2003 | Gellman |
| 2003/0191492 | A1 | | 10/2003 | Gellman et al. |
| 2003/0195456 | A1 | | 10/2003 | Robertson |
| 2003/0199805 | A1 | | 10/2003 | McWeeney |
| 2005/0049668 | A1 | * | 3/2005 | Jones et al. .................. 623/1.12 |
| 2005/0131547 | A1 | | 6/2005 | Segura et al. |
| 2007/0005125 | A1 | * | 1/2007 | Berenstein et al. .......... 623/1.15 |
| 2007/0021828 | A1 | * | 1/2007 | Krolik et al. ................. 623/1.31 |
| 2007/0213809 | A1 | * | 9/2007 | Weber .......................... 623/1.15 |
| 2009/0030363 | A1 | | 1/2009 | Gellman |
| 2009/0326641 | A1 | * | 12/2009 | Davis et al. .................. 623/1.15 |
| 2010/0076574 | A1 | | 3/2010 | Gellman |
| 2014/0142721 | A1 | * | 5/2014 | Robertson et al. ......... 623/23.66 |

OTHER PUBLICATIONS

Non Final Office Action for U.S. Appl. No. 12/241,450, mailed on Sep. 16, 2010, 13 pages.

Non-Final Office Action for U.S. Appl. No. 12/241,450, mailed on Oct. 6, 2014, 08 pages.

Final Office Action for U.S. Appl. No. 12/241,450, mailed on Mar. 4, 2014, 10 pages.

Final Office Action for U.S. Appl. No. 12/241,450, mailed on Feb. 25, 2014,10 pages.

Notice of Allowance for U.S. Appl. No. 12/241,450, mailed on Feb. 17, 2015, 08 pages.

Final Office Action for U.S. Appl. No. 12/241,450, mailed on Mar. 10, 2011, 14 pages.

Non-Final Office Action for U.S. Appl. No. 12/241,450, mailed on Oct. 31, 2013,13 pages.

Advisory Action for U.S. Appl. No. 12/241,450, mailed on May 19, 2011, 3 pages.

Requirement for Restriction/Election for U.S. Appl. No. 12/241,450 mailed on Jun. 22, 2010, 6 pages.

Response to Non-Final Office Action for U.S. Appl. No. 12/241,450, filed Jan. 6, 2015, 9 pages.

Response to Final Office Action with RCE for U.S. Appl. No. 12/241,450, filed May 2, 2014, 10 pages.

Response to Non Final Office Action for U.S. Appl. No. 12/241,450, filed Jan. 21, 2011, 10 pages.

Response to Non Final Office Action for U.S. Appl. No. 12/241,450, filed Jan. 21, 2014, 9 pages.

Response to restriction requirement for U.S. Appl. No. 12/241,450, filed Jan. 21, 2014, 9 Pages.

Final Office Action for U.S. Appl. No. 12/628,289, mailed on Feb. 4, 2015, 18 pages.

Final Office Action for U.S. Appl. No. 12/628,289, mailed on Mar. 4, 2014,12 pages.

Non-Final Office Action for U.S. Appl. No. 12/628,289, mailed on Oct. 10, 2014, 17 pages.

Final Office Action for U.S. Appl. No. 12/628,289, mailed on May 9, 2012, 15 pages.

Non Final Office Action for U.S. Appl. No. 12/628,289, mailed on Jan. 13, 2012, 23 pages.

Non-Final Office Action for U.S. Appl. No. 12/628,289, mailed on Nov. 4, 2013, 13 pages.

Advisory Action for U.S. Appl. No. 12/628,289, mailed on Apr. 14, 2015, 3 pages.

Response to Final Office Action for U.S. Appl. No. 12/628,289, filed May 2, 2014, 12 Pages.

Restriction Required for U.S. Appl. No. 12/628,289, mailed on Nov. 1, 2011, 6 pages.

Response to Non Final Office Action for U.S. Appl. No. 12/628,289, filed Apr. 9, 2012, 12 Pages.

Response to Final Office Action for U.S. Appl. No. 12/628,289, filed Jul. 10, 2012, 11 Pages.

Response to Non Final Office Action for U.S. Appl. No. 12/628,289, filed Feb. 4, 2014, 11 Pages.

Response to Non Final Office Action for U.S. Appl. No. 12/628,289, filed Apr. 1, 2015, 12 Pages.

Response to Non Final Office Action for U.S. Appl. No. 12/628,289, filed Jan. 9, 2015, 13 Pages.

Mardis et al., "Ureteral Stents", Urologic Clinics of North America, vol. 15, No. 3, Aug. 1988, pp. 471-479.

(56) References Cited

OTHER PUBLICATIONS

Barwart et al., "An Evaluation of the Transition Temperature Range of Super-Elastic Orthodontic NiTi Springs Using Differential Scanning Calorimetry", European Journal of Orthodontics, vol. 21, 1999, pp. 497-502.

Duerig et al., "Superelastic Nitinol for Medical Devices", MDDI Medical Device and Diagnostic Industry News Products and Suppliers, Mar. 1, 1997, 10 pages.

Kulkarni et al., "A Critical Evaluation of the Indications and Long Term Results of the Application of MEMOKATH® 051", presented at the 2000 World Congress on Endourology at the Ashford and St. Peter's Hospital, 2000, 1 page.

Kulkarni et al., "An Analysis of the Cost Effectiveness of a New Thermo Expandable Ureteric Stent MEMOKATH® 051", presented at the 1999 World Congress on Endourology at the Ashford Hospital, 1999, 1 page.

* cited by examiner

300

Insert a delivery member into a lumen defined by an elongate member — 310

Expand the delivery member — 320

Insert the delivery member into a body of a patient while the delivery member is in its expanded configuration — 330

Collapse the delivery member — 340

Remove the delivery member from the body of the patient — 350

DELIVERY DEVICE

CROSS-REFERENCE TO RELATED APPLICATION

This application is a Nonprovisional of, and claims priority to, U.S. Patent Application No. 61/691,012, filed on Aug. 20, 2012, entitled "DELIVERY DEVICE", which is incorporated by reference herein in its entirety.

TECHNICAL FIELD

This disclosure relates generally delivery devices for delivering a medical device, such as a stent or a catheter, to a location with a body of a patient.

BACKGROUND

A variety of medical procedures make use of medical devices that are placed into various locations within a body of a patient. For example, some medical procedures make use a stents or catheters that are configured to help facilitate the movement of fluid from one location within the body of the patient to another location within the body of the patient. In some cases, delivery devices are used to deliver or place the medical devises, such as stents or catheters, into position within the body of the patient.

Accordingly, there is a need for delivery devices that are configured to effectively and efficiently place medical devices within a body of a patient.

SUMMARY

In one embodiment, a medical device includes an elongate member and a delivery member. The elongate member has a retention portion and defines a lumen. The retention portion has a first configuration and a second configuration different than the first configuration. The retention portion is biased to the first configuration. The delivery member has a collapsed configuration and an expanded configuration. The delivery member is configured to be disposed within the lumen of the elongate member to move the retention portion of the elongate member from the first configuration to the second configuration.

In another embodiment, a medical device has an elongate member and a delivery member. The elongate member has a retention portion and defines a lumen. The delivery member, the delivery member having a collapsed configuration and an expanded configuration, the delivery member being configured to be disposed within the lumen of the elongate member, the delivery member having an outer surface, the outer surface of the delivery member is configured to be coupled to an inner surface of the elongate member when the delivery member is disposed within the lumen of the elongate member and the delivery member is in its expanded configuration.

In another embodiment, a method of placing an elongate member into a body of a patient includes expanding a delivery member from a first configuration to a second configuration to couple an elongate member to the delivery member; inserting the delivery member into a body of a patient while the elongate member is coupled to the delivery member; collapsing the delivery member from the second configuration to the first configuration; and removing the delivery member from the body of the patient.

DETAILED DESCRIPTION

The devices and methods described herein are generally directed to medical devices. In some embodiments, the medical devices include an elongate member that can be inserted into a body of a patient and used to help promote or facilitate the flow of fluid from one portion of the body to another portion of the body. For example, in some embodiments, a stent or a catheter may be placed within the body of a patient. The stent or the catheter may help facilitate flow of fluid, such as body fluid or other fluids, from one location within the body of the patient to another location within the body of the patient or to a location outside of the body of the patient. In some embodiments, the medical devices include a delivery tool that can be used to facilitate the placement of the elongate member within the body of the patient.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of an insertion tool or device as described herein refers to the end or portion of the device that is first inserted into a body of a patient during a medical procedure. The proximal end or portion is the end or portion of the device that is remains outside of the body of the patient during the insertion procedure (or if the entire device is inserted into the body of the patient during the delivery procedure, the proximal end portion is inserted into a body of the patient after the distal end or distal portion is inserted).

Figure 1:
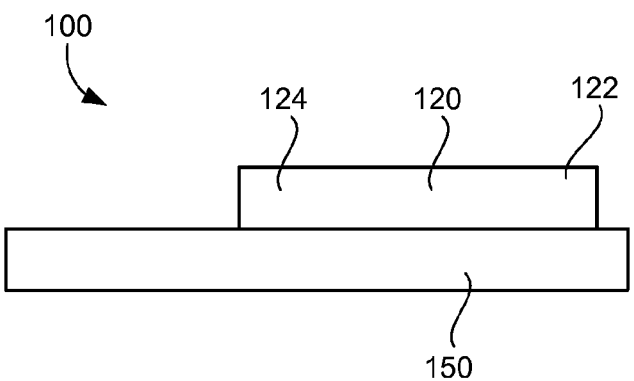
FIG. 1 is a schematic illustration of a medical device according to an embodiment.

FIG. 1 is a schematic illustrate of a medical device 100 according to an embodiment of the invention. The medical device 100 includes an elongate member 120 and a delivery device 150. The elongate member 120 is configured to be placed within a body of a patient. The delivery device 150 is configured to be removably coupled to the elongate member 120 and facilitate the delivery and placement of the elongate member 120 within the body of the patient.

In some embodiments, the elongate member 120 is a device that may be placed within a body of a patient to help retain patency of a bodily lumen or may help facilitate movement of fluid within the body of the patient. For example, in some embodiments, the elongate member is a stent or a catheter. In some embodiments, the elongate member is a stent or a catheter that may be placed within a urinary tract of a patient.

In some embodiments, the elongate member 120 includes a proximal end portion 122 and a distal end portion 124. In some embodiments, the elongate member 120 defines a lumen that extends from the proximal end portion 122 to the distal end portion 124. In some embodiments, the elongate member 120 is configured such that the distal end portion 124 of the elongate member 120 may be placed within a kidney of the patient and the proximal end portion 122 of the elongate member 120 may be placed within the ureter or bladder of the patient. In such embodiments, the elongate member 120 may help facilitate the flow of fluid (such as urine or other bodily fluids) from the kidney of the patient to the bladder of the patient. In other embodiments, the elongate member may be a device used to treat other bodily lumens or ducts, such as, but not limited to, the biliary duct and the pancreatic duct.

In some embodiments, the elongate member 120 includes retention members or portions. For example, in some embodiments, the retention members or portions are configured to help retain the elongate member 120 in place within the body of the patient. In some embodiments, the retention members or portions include curled portions, loop portions, pigtail portions, helical portions, J-hook portions, or any other shaped portions that would help retain the elongate member 120 within the body of the patient. In some embodiments, the retention member or portion is biased to its non-linear or retention shape. In other words, in some embodiments, the elongate member 120 may be placed within the body of the patient while the retention member or portion is in an linear configuration and then once in place the retention member or portion may assume (and is biased to) its non-linear or retention shape.

In some embodiments, the distal end portion 124 of the elongate member 120 includes a retention member or portion. In some embodiments, the proximal end portion 122 of the elongate member 120 includes a retention member or portion. In other embodiments, both the distal end portion 124 and the proximal end portion 122 include retention members or portions.

In some embodiments, the elongate member 120 includes a plurality of coils that define the lumen. In other embodiments, the elongate member 120 has a sidewall that defines the lumen. In some embodiments, the sidewall defines helical or spiral opening. In such embodiments, the turns or coils of the sidewall define the lumen.

The delivery device or member 150 is a device that is configured to be removably coupled to the elongate member and is configured to facilitate the insertion and placement of the elongate member within the body of the patient. For example, in some embodiments, the delivery member 150 is configured to be coupled to the elongate member. For example, in some embodiments, the delivery member 150 may include an inflatable portion that is configured to be inflated to couple the delivery member 150 to the elongate member. In other embodiments, the delivery member 150 includes a coupler that may be activated to engage the elongate member to couple the delivery member 150 to the elongate member. The delivery member 150 (or at least a portion of the delivery member 150), while coupled to the elongate member 120, may be inserted into the body of the patient. Once the elongate member 120 is placed in the correct position within the body of the patient, the delivery member 150 can be detached or removed from the elongate member 120 and removed from the body. This process leaves the elongate member 120 in place within the body of the patient.

In some embodiments, the delivery member 150 has an expanded or inflated configuration and a collapsed or deflated configuration. In such embodiments, the delivery member 150 may be inflated or expanded to couple the delivery member 150 (such as an outer surface of the delivery member 150) to the elongate member 120 (such as an inner surface of the elongate member 120). The delivery member 150 may then be collapsed or deflated to remove or decouple the delivery member 150 from the elongate member 120.

In some embodiments, the delivery member 150 is configured to be inflated with a liquid, gas, or fluid. For example, in some embodiments, the delivery member 150 includes an inflation chamber that may be filled or expanded to place the delivery member 150 in its expanded configuration or emptied to place the delivery member 150 in its deflated or collapsed configuration. In some embodiments, the delivery member 150 defines or includes an inflation lumen that is in fluid communication with the inflation chamber and is configured to deliver liquid, fluid, or gas to the inflation chamber (to inflate or expand the delivery member) and is configured to convey liquid, fluid, or gas out of the inflation chamber (to deflate or collapse the delivery member). In some embodiments, the delivery member 150 may be placed in the expanded configuration due to elastic deformation.

Figure 2:
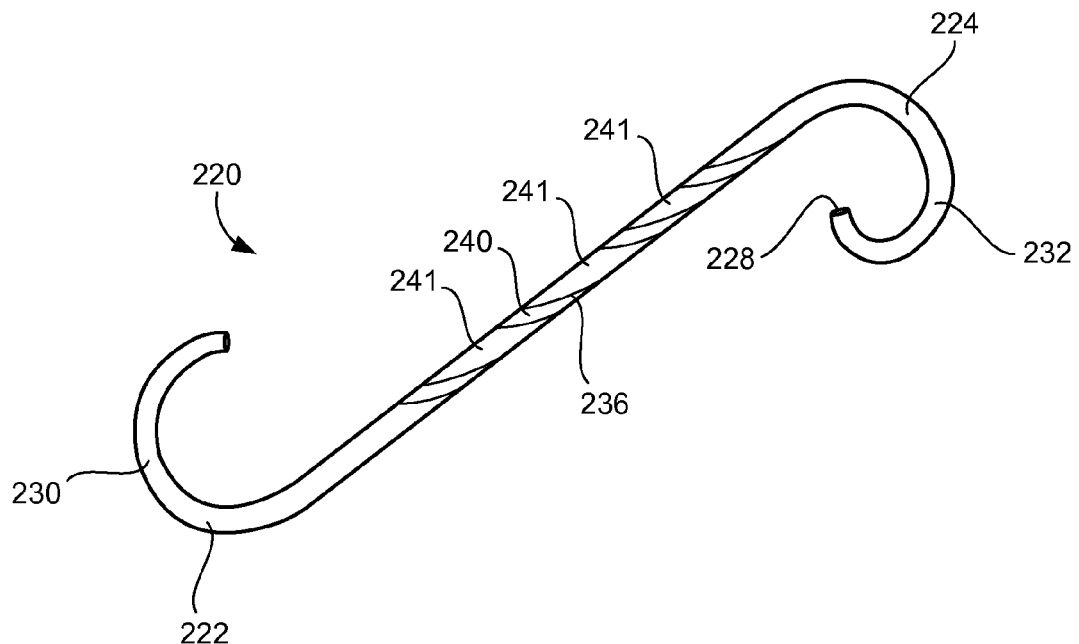
FIG. 2 is a perspective view of an elongate member according to an embodiment.

FIG. 2 is a perspective view of an elongate member 220 according to an embodiment. The elongate member 220 is a device that may be placed within a body of a patient to help retain patency of a bodily lumen or may help facilitate movement of fluid within the body of the patient. Specifically, in some embodiments, the elongate member 220 is a stent or a catheter and may be placed within a urinary tract of a patient. In the illustrated embodiment, the elongate member 220 defines a lumen 228. The lumen 228 is configured to help convey fluid within the body of the patient.

The elongate member 220 includes a proximal end portion 222 and a distal end portion 224. The elongate member 220 defines a lumen 228 that extends from the proximal end portion 222 to the distal end portion 224. The elongate member 220 is configured such that the distal end portion 224 of the elongate member 220 may be placed within a kidney of the patient and the proximal end portion 222 of the elongate member 220 may be placed within the ureter or bladder of the patient. The elongate member 220 may help facilitate the flow of fluid (such as urine or other bodily fluids) from the kidney of the patient to the bladder of the patient. In other embodiments, the elongate member 220 may be used to facilitate flow of fluid in other parts of a patients body, such as through other ducts or lumens.

The elongate member 220 includes retention members or portions 230 and 232. The retention members or portions 230 and 232 are configured to help retain the elongate member 220 in place within the body of the patient. Specifically, in the illustrated embodiment, the retention member 230 is disposed at the proximal end portion 222 and the retention member 232 is disposed at the distal end portion 224. The retention portion 230 is configured to be disposed within the bladder of the patient and to help retain at least a portion of the elongate member 220 within the bladder of the patient. The retention portion 232 is disposed at the distal end portion 224 of the elongate member 220. The retention portion 232 is configured to be disposed within the kidney of the patient and is configured to help retain at least a portion of the elongate member 220 within the kidney of the patient.

In the illustrated embodiment, the elongate member 220 is substantially linear and the retention members or portions 230 and 232 include non-linear portions. In some embodiments, the retention members or portion 230 and 232 may be non-linear and may include one or more linear portions or segments. Specifically, the retention portions 230 and 232 include curled portions. In other embodiments, the retention portions include non-linear portions of different shapes. For example, in some embodiments, the retention members or portions include pigtail portions, looped portions, helical portions, J-hook portions, or any other shaped portion that would help retain the elongate member 220 within the body of the patient.

In the illustrated embodiment, the elongate member 220 (or a sidewall of the elongate member) defines a helical opening 240. Coils or loops of the elongate member 220 (formed by the helical opening 240) define a portion of the lumen 228. In other embodiments, the elongate member 220 defines different shaped openings along its length. In further embodiments, the elongate member 220 does not define additional openings along its length.

In some embodiments, the elongate member 220 may be formed using an extrusion process, a molding process, or a machining process. In other embodiments, the elongate member 220 is formed using a different process. In some embodiments, the elongate member 220 is formed of a biocompatible polymer material. In other embodiments, the elongate member 220 is formed of a different material, such as another biocompatible material, including a metal material.

Figure 5:
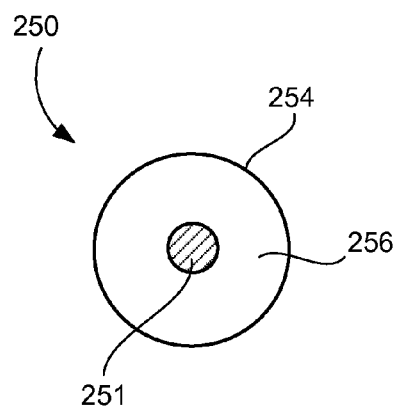
FIG. 5 is a cross-sectional view of the deliver device of FIG. 3 taken along line B-B of FIG. 3.

As illustrated in FIG. 5 and described in more detail below, the retention members or portions 230 and 232 are configured to be placed in a linear configuration for insertion and placement of the elongate member 220 into the body of the patient. Once the elongate member 220 is placed and positioned within the body of the patient, the retention members or portions 230 and 232 may be moved (or allowed to bias) back to their non-linear configurations.

Figure 3:
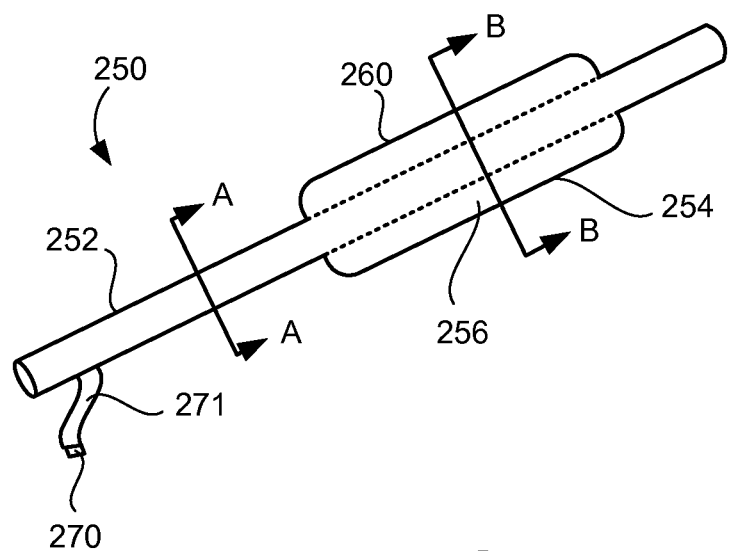
FIG. 3 is a perspective view of a delivery device according to an embodiment.
Figure 4:
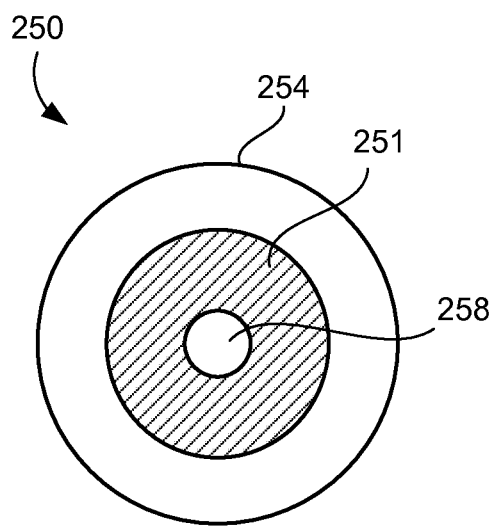
FIG. 4 is a cross-sectional view of the delivery member or device of FIG. 3 taken along line A-A of FIG. 3.

FIG. 3 is a perspective view of a delivery device 250 according to an embodiment. FIG. 4 is a cross-sectional view of the delivery device 250 taken along line A-A of FIG. 3. The delivery device or member 250 is a device that is configured to be removably coupled to the elongate member and is configured to facilitate the insertion and placement of the elongate member within the body of the patient. For example, in some embodiments, the delivery member 250 is configured to be coupled to the elongate member. The delivery member 250 (or at least a portion of the delivery member 250) while coupled to the elongate member 220 may be inserted into the body of the patient.

In the illustrated embodiment, the delivery member 250 includes a handle portion 252. The handle portion 252 is configured to be grasped by a user of the device, such as a physician, to insert and place the device within the body of the patient. In some embodiments, the handle portion 252 is configured to remain outside of the body of the patient. Once the elongate member 220 is placed in the correct position within the body of the patient, the delivery member 250 can be detached or removed from the elongate member 220 and removed from the body. This process leaves the elongate member 220 in place within the body of the patient.

The delivery member 250 includes an expandable or inflatable portion 260. The delivery member 250, or the expandable or inflatable portion 260, has an expanded or inflated configuration and a collapsed or deflated configuration, as illustrated in FIGS. 3 and 4. The delivery member 250 may be inflated or expanded to couple the delivery member 250 (such as an outer surface 254 of the delivery member 250) to the elongate member 220 (such as an inner surface 236 of the elongate member 220). The delivery member 250 may then be collapsed or deflated to remove or decouple the delivery member 250 from the elongate member 220. In some embodiments, the expandable or inflatable portion 260 is formed of an elastic material that is configured to stretch when the delivery member 250 is placed in its expanded or inflated configuration. In other embodiments, the expandable or inflatable portion 260 is formed of a static material (i.e., material that is not configured to stretch or expand).

The delivery member 250 is configured to be inflated with a liquid, gas, or a fluid. The delivery member 250 includes an inflation chamber 256 that may be filled or expanded to place the delivery member 250 in its expanded configuration or emptied to place the delivery member 250 in its deflated or collapsed configuration. The delivery member 250 defines or includes an inflation lumen 258 that is in fluid communication with the inflation chamber 256 and is configured to deliver fluid or gas to the inflation chamber 256 and is configured to convey fluid or gas out of the inflation chamber 256.

As best illustrated in FIG. 5, the inflation chamber 256 is concentrically disposed about a shaft portion 251 of the delivery device 250. In other embodiments, the delivery device 250 includes an inflation chamber that is disposed along one side of the shaft portion 251 of the delivery device 250. In some embodiments, the delivery device 250 includes a coating or outer layer that includes a friction limiting component. For example, the delivery device 250 may include a coating that limits the friction between the delivery device 250 and the elongate member 220.

In the illustrated embodiment, the delivery member 250 includes a stem portion 271. The stem portion 271 includes a coupler 270. The stem portion 271 extends from an elongate portion of the deliver member 250 and defines a lumen. The lumen is in fluid communication with the inflation lumen 258. The coupler 270 is operatively coupled to the inflation lumen 258 and is configured to be removably coupled to a device that is configured to deliver to or receive fluid from the inflation lumen 258 and the inflation chamber 256. For example, in some embodiments, the coupler 270 includes a luer lock or other screw type portion that is configured to removably couple the coupler to a device configured to deliver fluid.

In some embodiments, the delivery member 250 includes a valve. The valve is configured to help retain the fluid in place within the inflation chamber 256 to help keep the delivery member 250 in its expanded or inflated configuration. In some embodiments, the valve may be located within the inflation lumen 258 or within the coupler 270. In some embodiments, the device configured to deliver the fluid to the inflation lumen 258 includes a valve or is otherwise configured to help retain the fluid within the inflation chamber 256 (for example, by keeping a pressure on the fluid disposed within the inflation chamber 256).

In the illustrated embodiment, the delivery member 250 is a solid, relatively stiff (stiffer than the elongate member 220), cylindrical member. In other embodiments, the delivery member 250 is flexible. Accordingly, in some embodiments, the delivery member 250 may be used to deliver and place the elongate member 220 into the body of the patient without the use of an additional member or tool, such as a guidewire.

In other embodiments, the delivery member 250 may define a central lumen that is configured to receive another tool or member, such as a guidewire or a dilator. In such embodiments, the delivery member 250 may be configured to be moved or slid along the guidewire to place the elongate member 220 into the body of the patient. The delivery member 250 may be formed of a biocompatible polymer material or any other type of biocompatible material.

In some embodiments, the expandable portion 260 of the delivery member 250 is an expandable basket or cage. The expandable basket or cage may be expanded by pushing or forcing a proximal end of the delivery member 250 towards a distal end of the delivery member 250. In other embodiments, the expandable portion may expand by elastic expansion.

In some embodiments, the portion of the delivery member 250 that contacts the elongate member 220 is not a large or as long as illustrated. For example, in some embodiments, the expandable portion or contact portion of the delivery member 250 is shorter or has a length that is shorter than the length of the elongate member 220. In some embodiments, the portion of the delivery member 250 that contacts the elongate member 220 is a point and is sufficiently long to hold or retain the coils straight.

Figure 6:
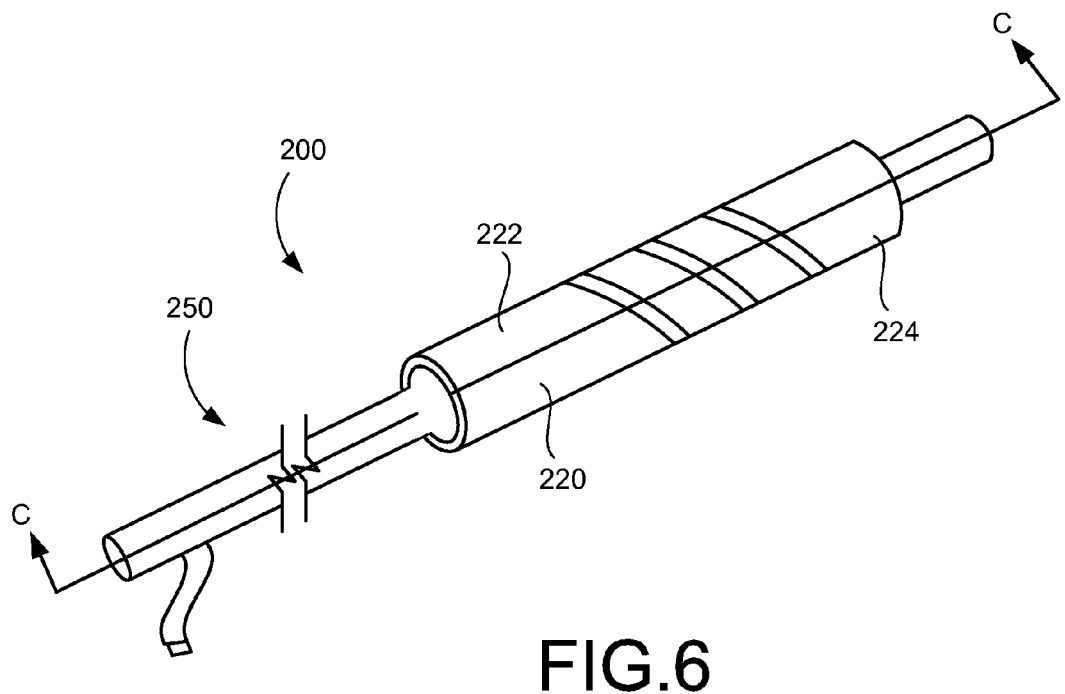
FIG. 6 is a perspective view of the delivery device of FIG. 3 disposed within the elongate member of FIG. 2.

FIG. 6 is a perspective view of a medical device 200 that includes a delivery device 250 and an elongate member 220. The delivery device 250 is disposed within the elongate member 220. Specifically, the delivery device 250 is disposed within and extends through a lumen 228 defined by the elongate member 220. The delivery device 250 extends along a longitudinal axis is a substantially linear manner. The delivery device 250 is relatively rigid (i.e., more rigid than the elongate member 220) and thus, when disposed within the lumen of the elongate member 220 forces the elongate member 220 to confirm to a linear configuration as well. Specifically, the retention portions 230 and 232, which include portions biased to curved configurations, are disposed in substantially linear configurations when the delivery member 250 is disposed within the lumen 228 defined by the elongate member 220.

Figure 7:
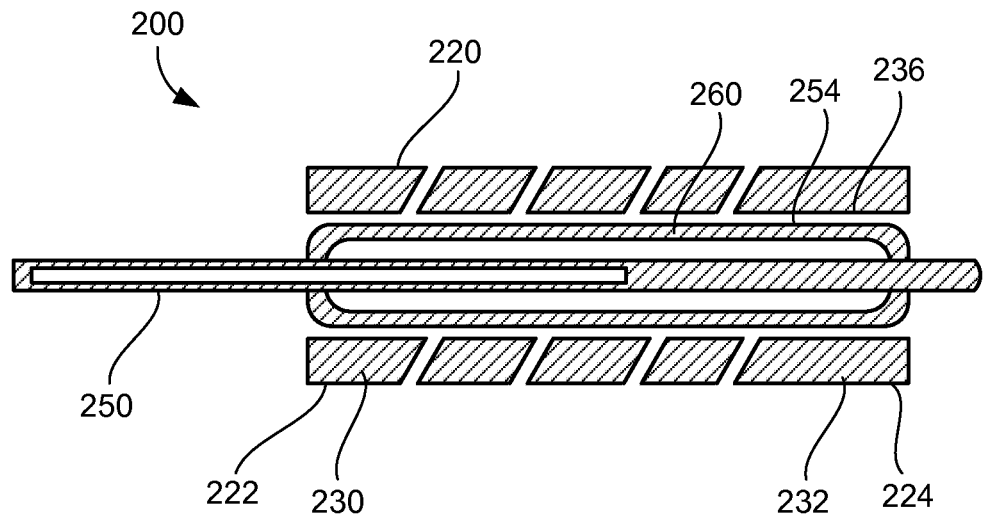
FIG. 7 is a cross-sectional view of the delivery device of FIG. 3 disposed within the elongate member of FIG. 2 taken along line C-C of FIG. 6.

FIG. 7 is a cross-sectional view of the medical device 200 taken along line C-C of FIG. 6. In FIGS. 6 and 7, the delivery device 250 is disposed within and coupled to the elongate member 220. Specifically, the delivery device 250 is disposed in its expanded or inflated configuration and an outer surface 254 of the delivery device 250 is coupled to the inner surface 236 of the elongate member 220. In the illustrated embodiment, the outer surface 254 of the delivery device 250 is frictionally coupled to the inner surface 236 of the elongate member 220. In some embodiments, a size of the expanded or inflated delivery device 250 (such as the outside diameter of an expanded portion of the delivery device 250) is larger than a size of the elongate member 220 (such as the inner diameter of the elongate member 220). The force of the delivery device 250 against the elongate member 220 frictionally couples the delivery device 250 to the elongate member 220.

With the delivery device 250 coupled to the elongate member 220, the medical device 200 may be inserted into and positioned within a body of a patient. For example, while being inserted the coupling of the delivery member 250 to the elongate member 220 (such as the frictional force or coupling), retains the elongate member 220 in place on the delivery device 250. In other words, as the device 200 is inserted into the body, the force against the elongate member 220 does not cause the elongate member 220 to become decoupled or move with respect to the delivery device 250.

In some embodiments, while the medical device 200 is disposed outside of the body of the patient and in preparation of delivering the medical device to a treatment site within the patient, the delivery device 250 can be inserted into the lumen 228 defined by the elongate member 220 while the delivery device 250 is in its collapsed or unexpanded configuration. The delivery device 250 can then be expanded or inflated. Specifically, a fluid, such as air or any other gas or water or any other liquid, may be inserted into the inflation chamber 256 to inflate or expand the expandable portion 260 of the delivery device 250. The delivery device 250 is then in its expanded configuration and is coupled to the elongate member 220. The device 200 can then be placed or inserted into the body of the patient.

Figure 8:
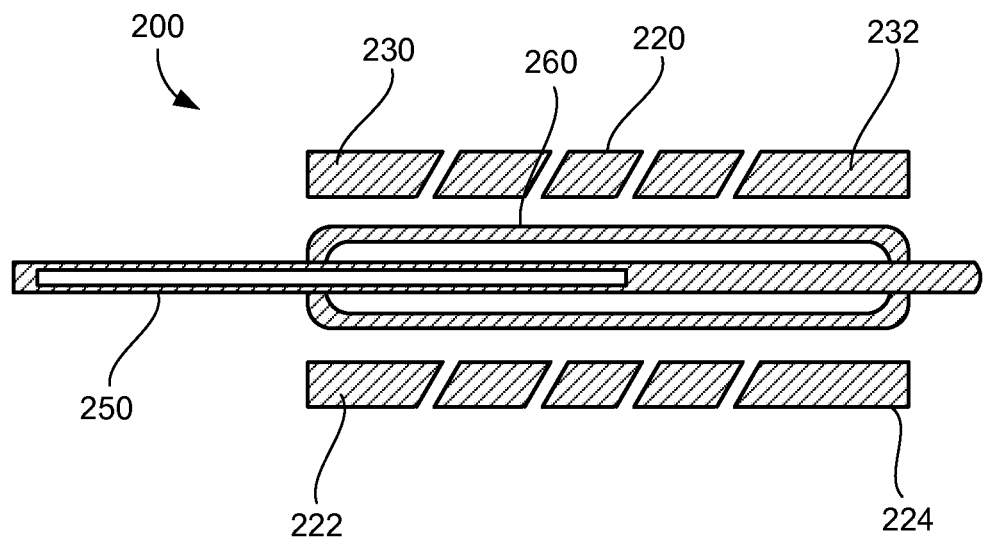
FIG. 8 is a cross-sectional view of the delivery device of FIG. 3 disposed within the elongate member of FIG. 2.

FIG. 8 is a cross-sectional view of the insertion device 250 disposed within the elongate member 220 while the insertion device 250 is in its collapsed or deflated configuration. In this configuration, the insertion device 250 is not coupled to the elongate member 220. Specifically, in the illustrated embodiment, the outer surface 254 of the delivery device 250 is not in contact with or is not frictionally coupled to the inner surface 236 of the elongate member 220. In this configuration, the delivery device may be removed from the lumen 228 defined by the elongate member 220.

In some embodiments, once the device 200 is inserted within the body of the patient and placed in the proper location, the delivery device 250 may be deflated and therefor decoupled from the elongate member 220. The delivery device 250 may then be removed from the elongate member 220 and the body of the patient. In some embodiments, this process leaves the elongated member 220 in place within the body of the patient. Additionally, once the delivery device 250 is removed from the lumen 228 of the elongate member 220 the retention members or portions 230 and 232 of the elongate member 220 return to their curved or retaining state (as they are biased to such configurations).

Figure 9:
FIG. 9 is a flow chart of a method according to an embodiment.

FIG. 9 is a flow chart of a method 300 of placing an elongate member within a body of a patient according to an embodiment. At 310, a delivery member is inserted into a lumen defined by the elongate member. In some embodiments, the insertion of the delivery member into the lumen of the elongate member forces or causes curved or non-linear retention members or portions to assume a substantially linear configuration. At 320, the delivery member is expanded to a larger or inflated configuration. In some embodiments, the expansion includes inflating or filling an inflation portion or inflation chamber of the delivery member with a fluid such as a liquid or a gas. In some embodiments, the inflating or expanding includes filling the inflation chamber via an inflation lumen defined by the delivery member.

In some embodiments, the inflation or expansion of the delivery member couples the delivery member to the elongate member. For example, in some embodiments, the inflation or expansion frictionally couples an outer surface of the delivery member to an inner surface of the elongate member.

At 330, the delivery member, while in its expanded configuration and while coupled to the elongate member, is inserted into a body of a patient. The coupling of the delivery member to the elongate member retains the elongate member in place with respect to the delivery member while the device is being inserted into the body of the patient. In some embodiments, the delivery member is used to place the elongate member into a urinary tract of a patient. For example, in some embodiments, the delivery member is used to insert the elongate member into a body of the patient such that a portion of the elongate member is disposed in a kidney of a patient and a portion of the elongate member is disposed in a ureter or bladder of the patient.

At 340, the delivery member is collapsed or moved to its smaller configuration. In some embodiments, the delivery member is collapsed or moved to its smaller configuration by removing the fluid, the liquid or the gas, from the inflation chamber. In some embodiments, the collapsing of the delivery member causes the delivery member to be decoupled or removed from the elongate member.

At 350, the delivery member is removed from the body of the patient. In some embodiments, this removal of the delivery member from the body of the patient leaves the elongate member in place within the body of the patient. In some embodiments, the removal of the delivery member includes removing the delivery member from the lumen defined by the elongate member. In such embodiments, once the delivery member is removed from the lumen of the elongate member, the retention members or portions of the elongate member assume their non-linear or biased shape.

In some embodiments, a medical device includes an elongate member having a retention portion and defining a lumen, the retention portion having a first configuration and a second configuration different than the first configuration, the retention portion being biased to the first configuration; and a delivery member, the delivery member having a collapsed configuration and an expanded configuration, the delivery member being configured to be disposed within the lumen of the elongate member to move the retention portion of the elongate member from the first configuration to the second configuration.

In some embodiments, the delivery member has an outer surface, the outer surface of the delivery member is configured to be coupled to an inner surface of the elongate member when the delivery member is disposed within the lumen of the elongate member and the delivery member is in its expanded configuration. In some embodiments, the elongate member has a sidewall, the sidewall of the elongate member defines a helical opening. In some embodiments, the elongate member has a coil portion, the coil portion including a plurality of coils. In some embodiments, the delivery member includes an inflation chamber and an inflation lumen, the inflation lumen being in fluid communication with the inflation chamber.

In some embodiments, a medical device includes an elongate member having a retention portion and defining a lumen; and a delivery member, the delivery member having a collapsed configuration and an expanded configuration, the delivery member being configured to be disposed within the lumen of the elongate member, the delivery member having an outer surface, the outer surface of the delivery member is configured to be coupled to an inner surface of the elongate member when the delivery member is disposed within the lumen of the elongate member and the delivery member is in its expanded configuration.

In some embodiments, the outer surface of the delivery member is configured to be frictionally coupled to the inner surface of the elongate member. In some embodiments, the elongate member has a sidewall, the sidewall of the elongate member defines a helical opening. In some embodiments, the elongate member has a coil portion, the coil portion including a plurality of coils.

In some embodiments, a method of placing an elongate member into a body of a patient includes expanding a delivery member from a first configuration to a second configuration to couple an elongate member to the delivery member; inserting the delivery member into a body of a patient while the elongate member is coupled to the delivery member; collapsing the delivery member from the second configuration to the first configuration; and removing the delivery member from the body of the patient.

In some embodiments, the expanding the delivery member includes inflating a portion of the delivery member. In some embodiments, the expanding the delivery member includes inflating a portion of the delivery member via an inflation lumen of the delivery member.

In some embodiments, the method includes inserting at least a portion of the delivery member into a lumen defined by the elongate member.

In some embodiments, the expanding the delivery member from the first configuration to the second configuration frictionally couples the elongate member to an outer surface of the delivery member. In some embodiments, the expanding the delivery member from the first configuration to the second configuration frictionally couples at least a portion of an inner surface of the elongate member to at least a portion of an outer surface of the delivery member. In some embodiments, the elongate member includes a coil portion that defines a lumen, the method further includes inserting at least a portion of the delivery member into at least a portion of the lumen defined bye the coil portion of the elongate member prior to the expanding the delivery member from the first configuration to the second configuration. In some embodiments, the delivery member has a first size in the first configuration and a second size in the second configuration, the first size being greater than the second size. In some embodiments, the collapsing the delivery member from second configuration to the first configuration decouples the elongate member from the delivery member. In some embodiments, the elongate member includes a retention member. In some embodiments, the elongate member defines a helical opening.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A method of placing an elongate member into a body of a patient, comprising:
    expanding a delivery member from a deflated configuration to an expanded configuration to couple an elongate member to the delivery member, the elongate member including a biocompatible polymer material defining a spiral opening on a middle portion of the elongate member, the delivery member including an inflation lumen and an inflation portion having an inflation chamber, the inflation portion being inserted into a lumen of the elongate member, the inflation portion being expanded to contact an inner surface of the elongate member by transferring fluid into the inflation chamber of the inflation portion such that an outer surface of the inflation portion is frictionally coupled to the inner surface of the elongate member;
    inserting the delivery member into a body of a patient while the elongate member is coupled to the delivery member;
    collapsing the delivery member from the expanded configuration to the deflated configuration such that the inner surface of the elongate member is not frictionally coupled to the outer surface of the inflation portion of the delivery member; and
    removing the delivery member from the body of the patient.

2. The method of claim 1, wherein expanding the delivery member includes expanding an outer diameter of the delivery member to a size larger than an inner diameter of the elongate member.

3. The method of claim 1, wherein the delivery member includes a handle proximally extending from the inflation portion, the handle including a stem configured to receive the fluid, the inflation lumen extending from the stem to the inflation chamber of the inflation portion.

4. The method of claim 1, wherein the elongate member includes a first retention member on a distal end portion of the elongate member and a second retention member on a proximal end portion of the elongate member, the lumen of the elongate member extending through the first and second retention members, the first and second retention members being curved when the elongate member is not coupled to the delivery member, the first and second retention members being forced to a linear configuration when the delivery member is coupled to the elongate member and the delivery member is in the expanded configuration.

5. The method of claim 4, wherein the spiral opening defines a plurality of coils on the middle portion of the elongate member, the first and second retention members being devoid of coils.

6. The method of claim 4, wherein the distal end portion of the elongate member is disposed within a kidney of the patient, and the proximal end portion of the elongate member is disposed within a ureter or bladder of the patient.

7. A method of placing an elongate member into a body of a patient, comprising:

expanding a delivery member from a deflated configuration to an expanded configuration to couple an elongate member to the delivery member, the elongate member including a biocompatible polymer material defining a spiral opening on a middle portion of the elongate member, the delivery member including a shaft and an inflation portion, the inflation portion being disposed around a middle part of the shaft such that both ends of the shaft extend beyond the inflation portion, the inflation portion being inserted into a lumen of the elongate member, the inflation portion being expanded to contact an inner surface of the elongate member such that an outer surface of the inflation portion is frictionally coupled to the inner surface of the elongate member;

inserting the delivery member into a body of a patient while the elongate member is coupled to the delivery member;

collapsing the delivery member from the expanded configuration to the deflated configuration such that the inner surface of the elongate member is not frictionally coupled to the outer surface of the inflation portion of the delivery member; and removing the delivery member from the body of the patient.

8. The method of claim 1, wherein the elongate member includes a retention member.

9. A method of placing an elongate member into a body of a patient, comprising:

expanding a delivery member from a deflated configuration to an expanded configuration to couple an elongate member to the delivery member, the elongate member including a biocompatible polymer material defining a spiral opening on a middle portion of the elongate member, the delivery member including an inflation portion that includes a coating having a friction limiting component that limits the friction between the delivery member and the elongate member, the inflation portion being inserted into a lumen of the elongate member, the inflation portion being expanded to contact an inner surface of the elongate member such that an outer surface of the inflation portion is frictionally coupled to the inner surface of the elongate member;

inserting the delivery member into a body of a patient while the elongate member is coupled to the delivery member;

collapsing the delivery member from the expanded configuration to the deflated configuration such that the inner surface of the elongate member is not frictionally coupled to the outer surface of the inflation portion of the delivery member; and removing the delivery member from the body of the patient.

10. The method of claim 1, wherein the spiral opening defines a plurality of coils on the middle portion of the elongate member.

11. The method of claim 1, wherein a distal end portion of the elongate member is disposed within a kidney of the patient, and a proximal end portion of the elongate member is disposed within a ureter or bladder of the patient.

12. The method of claim 7, wherein expanding the delivery member includes expanding an outer diameter of the delivery member to a size larger than an inner diameter of the elongate member.

13. The method of claim 7, wherein the delivery member includes a handle proximally extending from the inflation portion, the handle including a stem.

14. The method of claim 9, wherein expanding the delivery member includes expanding an outer diameter of the delivery member to a size larger than an inner diameter of the elongate member.

15. The method of claim 9, wherein the delivery member includes a handle proximally extending from the inflation portion, the handle including a stem configured to receive the fluid, the inflation lumen extending from the stem to the inflation chamber of the inflation portion.

16. The method of claim 9, wherein the spiral opening defines a plurality of coils on the middle portion of the elongate member.

17. The method of claim 9, wherein a distal end portion of the elongate member is disposed within a kidney of the patient, and a proximal end portion of the elongate member is disposed within a ureter or bladder of the patient.

18. The method of claim 9, wherein the delivery member includes a shaft, the inflation portion being disposed around a middle part of the shaft such that both ends of the shaft extend beyond the inflation portion.

19. The method of claim 9, wherein the elongate member includes a retention member.

\* \* \* \* \*